United States Patent [19]

Packman et al.

[11] 4,234,566

[45] Nov. 18, 1980

[54] ANTIHISTAMINE AND METHODS FOR USE THEREOF

[76] Inventors: Elias W. Packman, 214 Sycamore Ave., Merion, Pa. 19066; Ruth Jeffkin, 259 Richards Ave., Lansdowne, Pa. 19050

[21] Appl. No.: 53,399

[22] Filed: Jun. 29, 1979

Related U.S. Application Data

[62] Division of Ser. No. 741,298, Nov. 12, 1976.

[51] Int. Cl.$^3$ .................. A61K 7/00; A61K 7/32; A61K 7/34; A61K 7/36
[52] U.S. Cl. .................................. 424/47; 424/45; 424/65; 424/66; 424/67; 424/68
[58] Field of Search ................. 424/47, 45, 65, 66, 424/67, 68

[56] References Cited

U.S. PATENT DOCUMENTS 3,624,200  11/1971  Moffgtt .................. 424/65

OTHER PUBLICATIONS

C.A. 52:11365(b) 1958.
C.A. 53:15348(e) 1959.
C.A. 53:19135(c) 1959.

*Primary Examiner*—Allen J. Robinson
*Attorney, Agent, or Firm*—Weiser, Stapler & Spivak

[57] ABSTRACT

Antiperspirant compositions containing antihistamines, such as diphenhydramine hydrochloride, alone or in combination with astringent metallic salts, as the active agent effective for retarding or inhibiting perspiration when topically applied to the human skin. Method for controlling or preventing perspiration in humans.

21 Claims, No Drawings

ANTIHISTAMINE AND METHODS FOR USE THEREOF

This is a division of application Ser. No. 741,298, filed Nov. 12, 1976.

This invention relates to antiperspirant formulations containing an antihistamine, alone or in combination with at least one astringent metallic salt, as an active ingredient and a method for controlling and preventing perspiration when applied topically to humans.

Eccrine sweat glands, which secrete copius liquid sweat, are activated through cholinergic fiber innervation, by acetylcholine, which is liberated at the stimulated nerve endings. Apocrine sweat glands are fewer in number and unlike the general distribution of eccrine glands, localized in areas such as the axillae. While the eccrine gland responds primarily to thermal stimuli, apocrine glands are responsive to muscular activity and emotional stimuli. The apocrines are thought to be responsive to andrenergic circulatory epinephrine only.

Traditionally, metal salts having astringent properties have been used to inhibit perspiration, particularly the astringent salts of aluminum, zinc, zirconium or rare earth metals. Such salts often require a number of applications over a period of time to reach a satisfactory level of antiperspirant activity. The salts tend to react with the skin, changing its chemical composition and halides of aluminum, perhaps the most widely used ingredient, possess other disadvantages such as axillary irritation, attributed to their low pH, fabric damage and fabric staining. These salts are thought to react with skin proteins, causing coagulation, swelling, and, thus, blockage of sweat glands in a nonselective manner. Difficulty in overcoming these drawbacks increases with the amount of astringent salt used. Also, as reported in U.S. Pat. No. 3,767,786, they are ineffective on some users.

The use of metallic salts exhibiting astringent action is exemplified by U.S. patents to MacMillan et al (U.S. Pat. No. 3,678,156); Wetzel et al (U.S. Pat. No. 3,555,145); Dobson et al (U.S. Pat. No. 3,499,916); Mummert (U.S. Pat. No. 3,395,214); Miechowski (U.S. Pat. No. 3,325,367); Abramson (U.S. Pat. No. 2,893,918); and Daley (U.S. Pat. No. 2,814,584).

It would be therefore desirable to be able to use these salts in amounts modest enough not to be objectionable, in the various ways discussed above.

The range of dosages which the prior art has disclosed as being effective for these metallic astringents has been 1-10% for aluminum chloride, aluminum sulfate or aluminum chlorhydroxide when in combination with 0.02%-0.5% of silver protein (U.S. Pat. No. 2,893,918) and 3% for zirconium or hafnium salt in combination with 2-20% aluminum salt (U.S. Pat. No. 2,814,584). Sprayable foams of 15-35% antiperspirant and aerosols of 6-15% are reported in U.S. Pat. Nos. 3,395,214 and 3,555,145. Apparently, in amounts less than those disclosed these salts are not adequately effective to control sweating.

Other antiperspirant compositions have been developed which, as disclosed in DeSalva et al (U.S. Pat. No. 3,755,538) use analgesics, hypotensive agents, local anesthetics and antispasmodics. Likewise, antiperspirant compositions containing sodium or lithium tetraarylboron compounds (Loomans, U.S. Pat. No. 3,726,968) and titanium compounds (Berger, U.S. Pat. No. 3,090,728) have been prepared.

U.S. Pat. No. 3,678,156 teaches that certain sulfoxides are useful to enhance penetration of pharmacologically active substances. Disclosed in the patent are conventional antiperspirants such as astringent metal salts (in amounts of 5 to 50 percent), anticholinergics, antimicrobials, antibiotics, anesthetics and also antihistamines. Metapyrilene hydrochloride with decyl methyl sulfoxide is suggested for treating allergic reactions. There is no disclosure nor suggestion to use an antihistamine for controlling perspiration, or that an antihistamine could possess such useful property.

Other attempts to inhibit sweating are known. Various anticholinergic agents have been employed as antiperspirants, principal ones being various esters of the Belladonna alkaloids scopolamine and atropine. Such esters are disclosed in U.S. Patents to MacMillan (U.S. Pat. Nos. 3,312,709; 3,325,768; 3,767,786) and Moffett (U.S. Pat. No. 3,624,200).

Although the potential utility of anticholinergic agents in cosmetic antiperspirant formulations has been recognized, such utilization has been retarded because the classic anticholinergics do not provide adequate control of perspiration at levels which are physiologically safe. Prior art has disclosed scopolamine esters to be virtually the only anticholinergic agents which have levels which are both safe and at the same time effective. These scopolamines esters, however, are known to have a tendency to hydrolyze and lose activity over protracted periods of time. Furthermore, there is the possibility of undesirable systemic side effects should such active ingredients be removed from the local area of application by the circulatory system.

It is evident that numerous attempts have been made to solve the problem of objectionable sweating and yet no satisfactory solution is available. There is a real need for a safe and effective product and treatment for preventing sweating.

The use of antihistamines as antipruritics has been known for the treatment of hypersensitivity reactions by topical application in such forms as ointments. (See Waldriff et al, *Archives of Dermatology and Syphilology.* 61;6 March 1950). This involves treatment of symptoms in areas of the body which are exposed to external immunogen agents, such as the face and exposed suface areas of the limbs where cases of "poison ivy" and the like are commonly evidenced. Typical antihistamines which have been reported as antipruritic include chlorpheniramine maleate, tripelennamine hydrochloride and methapyrilene hydrochloride. Such treatment with topical antihistamine preparations has not heretofore been directed to the prophylactic control of nonimmunological functions.

Compositions of the present invention, as disclosed herein, are effectively applied to normally unexposed areas of the body other than the axillae as well, such as the soles of the feet.

The compositions of the present invention comprises an antihistamine, or physiologically acceptable salt thereof, in combination with a pharmaceutically acceptable carrier. They are typically dispersed in a topical medium as the carrier of choice.

The invention provides a method for controlling sweating by topically administering to an area of a human body which has sweat glands, such as the axillae, an amount effective to control such perspiration of a composition which is safe and effective and includes as active ingredient an antihistamine. The antihistamine can be used, in accordance with the invention in conjunction with metal salts of the type discussed above.

The amounts in which these ingredients are used in accordance with the invention is noteworthy. Particularly, it has been noted that, in accordance with the invention, the metal salt is adequately effective against sweating when used jointly with the antihistamine, in amounts which normally were considered too low to be effective. This may be suggest a coaction or synergism of those two ingredients, though not a theory on which the invention is predicated. The invention also makes possible the use of the antihistamine in quite modest amounts. Another noteworthy aspect of the invention is the prolonged and extended protection which the application of the composition of the invention makes available. Indeed, it appears that applications following the first administration of the composition are equally if not more effective than the first. Often in topical application of medicaments, the skin tends to become less receptive to further applications so that applications must be repeated in increased amounts for effective treatments.

In the composition of the invention the antihistamine is present in an amount from 0.5% to 2% but it can be present in smaller amounts like 0.01% to less than 0.5% or in amounts over 2% to 10%.

In accordance with the invention various antihistamines, in general the traditional antihistamines effective against $H_1$ receptors, can be used in controlling excessive perspiration. Contemplated antihistamines in the present invention are among others: ethanolamines like diphenhydramine, dimenhydrinate and carbinoxamine; ethylenediamines like pyrilamine, tripelennamine, antazoline and methapyriline; alkylamines like chlorpheniramine and brompheniramine; phenothiazines like promethazine; piperazines like cyclizine and meclizine; and the following: dixylamine, phenyltoloxamine, thenyldiamine, thonzylamine, cyproheptadine, dimethindene, pyrrobutamine, triprolidene, antazoline and clemizole.

Preferred compositions of the invention include the following: diphenhydramine, chlorpheniramine and tripelennamine.

The antihistamines are listed in the National Formulary or United States Pharmacopeia, are available commercially, many over-the-counter, and are sold under various trade names such as those listed in the Physician's Desk Reference (30th Edition) 1976. Commercial availability and government approval of these compounds for use as antihistamines contribute to the utility of the present invention.

Salts of the antihistamines which are useful in the present invention include the salts of strong inorganic acids like sulfuric, hydrochloric, phosphoric and the like and of organic carboxylic (mono and poly) acids like acetic, maleic, etc.

The compositions of this invention use antihistamines to inhibit the secretion or excretion of substances which give rise to offensive odors. Of special importance is the extended period of time following a single application during which representative compositions have been found to remain effective in clinical testing. Other aspects of these embodiments of the invention will become apparent in the description which follows.

Another important embodiment of the invention is a composition including an antihistamine in combination with an astringent metal salt for effective inhibition or control of perspiration. A typical salt is aluminum chloride. While the salts which are used in accordance with the invention are generally the traditional salts discussed above, it will become apparent that their use, that could not be properly exploited heretofore, in conjunction with antihistamine, open new practical applications.

One such aspect is the amount of metal salt and the relative amounts of antihistamine. The amount of antihistamine or metal salt useful may vary under the circumstances such as ambient temperature and the skin surface area to which it is applied. What is noteworthy is that the compositions of this embodiment generally permit the metal salt concentration to be less than about 1% with the concentration effectively ranging from as little as from about 0.1% to about 1%. The compositions are effective, when the metal salts are present, in amount below that which is essentially noneffective to close pores, thus less than previously necessary for that effect of the metal salt.

In this embodiment of the invention, the composition can contain antihistamines which ranges from a perceptible amount to a maximum limited essentially only by reasons of economy. A preferred range of antihistamine concentration is from 0.01% to about 5% by weight of the antihistamine, preferably from 0.01% to 2%. This amount is less than that when the antihistamine is used alone, thus suggesting a mode of coaction with the metal salt heretofore apparently unobserved.

Astringent metal salts which are useful in the present invention are those disclosed in the prior art which for example include: aluminum salts, zinc salts or zirconium salts, alone or in combination. Many others can be used in the invention, and the patents discussed above are included herein by reference.

In other aspects the antiperspirant composition of the invention may contain conventional materials and ingredients and conform to pharmacologically accepted formulations.

To that effect, the antiperspirant composition of the invention should preferably be adjusted to a pH compatible with the skin and optimal for antihistamine activity, such as a pH from 3 to 6.5.

Carriers into which the active ingredients can be incorporated to produce satisfactory antiperspirant composition are those commonly employed for topical application of cosmetics or pharmaceuticals. Such carriers or vehicles include lotions, ointments, aerosols, water solutions, creams (preferably of the oil-in-water type), pulverulent mixtures, gelled sticks and the like. Depending on the physical nature of the vehicle or carrier employed, the method of this invention can be practiced by applying such compositions topically in any appropriate manner according to the particular type of carrier employed.

In preparing the desired pharmaceutical form of the present compositions, various additives, diluents and adjuvants can be utilized. These illustratively include perfumes, essential oils, surfactants, ointment type bases, higher fatty acids, propellants, thickening agents, humectants, deodorants, antibiotics, silicone-type fluids and solid diluents as is known in the art.

For illustration of U.S. patents disclosing pharmaceutically or dermatologically acceptable compositions reference is made to U.S. Pat. Nos. 3,767,786; 3,326,768; and those recited therein which are incorporated by reference.

The compositions of the invention were tested on human patients in accordance with traditional accepted procedures.

Two methods were used to test the effectiveness of the antiperspirant compositions of this invention and to illustrate their administration, and other compositions with which they were compared. The two methods were the "axilla" method and the "ambient air" method.

The axilla method involves direct measurement of the weight of perspiration secreted in the axilla. This test is a traditionally accepted test for perspiration since the axilla is the area of most practical importance in the inhibition of perspiration. The present method is somewhat similar to the axilla method disclosed in the U.S. Pat. No. 3,326,786 of Kilmer et al, in that both methods use a gravimetric measure of the amount of perspiration produced in the axilla to determine the antiperspirant effect. Compositions of the present invention, as disclosed herein, are effectively applied to normally unexposed areas of the body other than the axillae as well, such as the soles of the feet.

Men and women were enrolled as subjects for this test. They were required to abstain for the use of all antiperspirant materials for 14 days prior to and throughout the test period. Soap and water and/or deodorant preparations could be used, however, as desired. The test was performed in one five-day period.

Control collections were made on the first day of the test week and test materials applied after the control collections were made. The subjects were treated with the test materials on the second day of the test but no secretions were collected.

On the third, fourth and fifth days of the test week, applications of the test materials were made one hour prior to collection. The axillae were washed with a two percent soap solution and rinsed with tepid water prior to each application. Applications were made to both axillae of all subjects with the antihistamine containing compositions of the present invention being applied to one axilla and the control or non-antihistamine containing composition being applied to the other. Assignments of each sample to each subject for the test week were randomized. After application, the subjects equilibrated at room temperature (approximately 68 degrees F.) for one hour. Perspiration of the test subjects was then induced by seating the subjects in a room maintained at 102°±2° F. and at a relative humidity of about 35%. A recording wet bulb dry thermometer, as well as a recording electronic thermocouple was kept in the room during the collection procedures.

During the first 20 minutes of the stimulation period, the subjects held unweighed pads of "Webril" (nonwoven 4"×4" cotton padding fabric) in the axillae. This preliminary warm-up period was followed by one 20 minute collection period, during which the subjects held weighed 4"×4" Webril pads in their axillae. After the collection period, the pads were removed from the axillae and weighed to determine the amount of perspiration produced. The reduction in sweating produced by the antihistamine containing composition of the invention as compared to the non-antihistamine containing antiperspirant composition was obtained by fitting the results from the axilla method into the following formula:

Percent reduction in sweating = 100 × $\frac{\text{net gain control} - \text{net gain antihistamine}}{\text{net gain control}}$ The following examples are not limiting the invention but are merely illustrative thereof.

EXAMPLE 1

400 mg. solutions of witch hazel containing 1% diphenhydramine hydrochloride were compared for antiperspirant efficacy with a leading antiperspirant composition, identified by the trademark name Arrid Extra Dry, which is reported to be an aluminum chlorohydrate composition containing no active antihistamine compound, using the axilla method on human subjects. The results from this test are shown in Table 1 below.

The total number of subjects was 36. Subjects 1-18 were female and 19-36 were male. Control data from the first day of testing is shown in column A and column B under the heading "Day 1". Column A represents the net gain in milligrams of perspiration produced in the untreated antihistamine axilla of the subjects being tested, and column B represents the net gain in milligrams of the perspiration produced in the untreated Arrid axilla. As described above, the antiperspirant compositions to be compared were applied to the subjects on the second day of testing; however, no secretions were collected. Consequently, no data from the second day of testing appears in Table 1.

Column C under the heading "Day 3" represents the difference in milligrams of the net gain in perspiration between the axillae treated with the antihistamine containing composition and the non-antihistamine containing composition. A positive number indicates a greater reduction in perspiration produced by the axillae treated with the antihistamine containing composition of the invention. A negative (−) sign preceding the number indicates greater reduction in the perspiration produced by the axillae treated with the non-antihistamine containing composition. Column E under "Day 4" and column G under "Day 5" represent similar data obtained on those respective days of the test.

Column D under "Day 3" and columns F and H under "Day 4" and "Day 5" respectively represent the corresponding percentage of reduction in sweating for the difference between axillae treated with the antihistamine containing composition and the non-antihistamine containing composition.

TABLE 1

| | COMPARATIVE EFFECTIVENESS OF AXILLARY ANTIPERSPIRANTS | | | | | | | |
|---|---|---|---|---|---|---|---|---|
| | Day 1 | | Day 3 | | Day 4 | | Day 5 | |
| Subject No. | A mgs. | B mgs. | C mgs. | D % | E mgs. | F % | G mgs. | H % |
| 1 | 426 | 457 | 129 | 37.61 | 24 | 11.27 | 102 | 43.40 |
| 2 | 361 | 358 | 138 | 39.76 | 112 | 34.67 | 45 | 17.44 |
| 3 | 351 | 325 | 11 | 3.50 | 20 | 8.09 | 18 | 8.30 |
| 4 | 364 | 357 | 99 | 28.77 | 94 | 27.64 | 24 | 8.82 |
| 5 | 398 | 415 | 41 | 11.88 | 85 | 23.41 | 109 | 35.50 |
| 6 | 442 | 412 | 29 | 9.41 | 31 | 10.36 | 83 | 27.21 |
| 7 | 308 | 408 | 104 | 30.05 | 38 | 16.45 | 61 | 27.23 |
| 8 | 337 | 346 | 87 | 30.10 | 120 | 34.09 | 92 | 28.48 |

TABLE 1-continued
COMPARATIVE EFFECTIVENESS OF AXILLARY ANTIPERSPIRANTS

| Subject No. | Day 1 A mgs. | Day 1 B mgs. | Day 3 C mgs. | Day 3 D % | Day 4 E mgs. | Day 4 F % | Day 5 G mgs. | Day 5 H % |
|---|---|---|---|---|---|---|---|---|
| 9  | 318 | 317 | 75   | 27.17  | 75   | 28.73  | 104  | 37.01 |
| 10 | 446 | 420 | 96   | 32.76  | 95   | 34.92  | 66   | 29.46 |
| 11 | 328 | 345 | 39   | 13.63  | 61   | 22.76  | 40   | 14.13 |
| 12 | 519 | 529 | 130  | 29.47  | 104  | 34.78  | 60   | 26.31 |
| 13 | 406 | 430 | 95   | 27.22  | 107  | 29.72  | 77   | 23.12 |
| 14 | 359 | 309 | 57   | 19.32  | 111  | 32.64  | 87   | 29.59 |
| 15 | 400 | 328 | 53   | 16.01  | 55   | 19.03  | 60   | 23.43 |
| 16 | 405 | 592 | −114 | −51.35 | −135 | −59.21 | −.091 | −38.39 |
| 17 | 305 | 402 | 120  | 31.41  | 96   | 28.31  | 53   | 18.86 |
| 18 | 497 | 381 | 119  | 34.49  | 53   | 18.21  | 70   | 24.22 |
| 19 | 557 | 337 | 49   | 15.21  | 102  | 28.25  | −78  | 27.36 |
| 20 | 325 | 410 | 101  | 31.96  | 142  | 40.57  | 137  | 38.16 |
| 21 | 524 | 338 | 54   | 15.83  | 71   | 24.06  | 81   | 27.27 |
| 22 | 503 | 509 | 122  | 38.60  | 67   | 21.40  | 83   | 27.57 |
| 23 | 333 | 460 | 234  | 52.46  | 220  | 49.55  | 216  | 48.87 |
| 24 | 649 | 492 | −110 | 20.91  | −55  | 9.48   | −88  | 23.09 |
| 25 | 642 | 762 | 219  | 39.96  | 163  | 31.53  | 118  | 25.54 |
| 26 | 628 | 605 | 49   | 15.86  | 23   | 8.04   | 51   | 18.89 |
| 27 | 465 | 427 | 35   | 10.48  | 101  | 26.23  | 38   | 11.69 |
| 28 | 441 | 302 | 46   | 17.23  | 27   | 10.51  | 28   | 10.00 |
| 29 | 469 | 442 | −19  | 5.44   | 74   | 23.47  | 136  | 41.85 |
| 30 | 355 | 428 | 95   | 26.46  | 73   | 24.50  | 95   | 30.16 |
| 31 | 656 | 411 | 21   | 6.82   | 27   | 10.47  | 21   | 10.61 |
| 32 | 362 | 558 | 11   | 2.98   | 42   | 11.67  | 15   | 5.00 |
| 33 | 323 | 305 | 91   | 43.33  | 71   | 29.58  | 10   | 4.57 |
| 34 | 572 | 480 | 12   | 4.08   | 41   | 14.70  | 22   | 7.07 |
| 35 | 453 | 388 | 115  | 37.10  | 123  | 43.00  | 111  | 38.54 |
| 36 | 393 | 411 | 97   | 25.33  | 182  | 46.19  | 70   | 20.40 |

As product was applied to both axillae in the study, changes in the level of perspiration is estimated by using the control day as a base. The technique indicates both products significantly effective on all treatment days. Treatment Day 3/control ratios, the best for each product, average 0.531 for diphenhydramine hydrochloride and 0.704 for Arrid. The diphenhydramine hydrochloride/Arrid ratio, adjusted for the control period, averaged 0.752. Thirty-four of the thirty-six panelists experienced superior performance with diphenhydramine hydrochloride.

Number of panelists perspiring less on the antihistamine treated axillae, mean amounts perspired on dipehnhydramine hydrochloride (A) and Arrid (B) axillae, mean differences and mean A/B ratios appear in Table 2.

TABLE 2

| | n | n A < B | $\overline{A}$ | $\overline{B}$ | $\overline{\Delta}$ B − A | A/B |
|---|---|---|---|---|---|---|
| Control | 36 | 16 | 434.4 | 422.1 | 12.3 | 1.026 |
| Test 1 | 36 | 34 | 266.5 | 337.9 | 71.3 | .775 |
| 2 | 36 | 34 | 247.1 | 320.4 | 62.5 | .763 |
| 3 | 36 | 34 | 231.4 | 295.0 | 56.1 | .775 |
| Average Test | 36 | 34 | 248.3 | 317.8 | 69.2 | .771 |
| Average Test/ Control | 36 | 34 | | | 81.7 | .752 |

All thirty-six panelists experienced a reduction in perspiration with both products. Day 3 proved significantly more effective than Day 1 for the antihistamine containing compositions and than Days 1 and 2 for Arrid. Treatment Day 3/control ratios averaged 0.531 for diphenhydramine hydrochloride and 0.704 for Arrid. A more detailed summary is provided in Table 3.

TABLE 3

| Diphenhydramine hydrochloride/Control | | | | | | |
|---|---|---|---|---|---|---|
| | n | n A < C | $\overline{A}$ | $\overline{C}$ | $\overline{\Delta}$ C − A | A/C |
| Treatment Day | 1 | 36 | 26 | 266.5 | 434.4 | 167.9 | .608 |
| | 2 | 36 | 36 | 247.1 | 434.4 | 187.4 | .564 |
| | 3 | 36 | 36 | 231.4 | 434.4 | 203.0 | .531 |
| Average | | 36 | 36 | 248.3 | 434.4 | 186.1 | .567 |

| Arrid/Control | | | | | | |
|---|---|---|---|---|---|---|
| | n | n B < C | $\overline{B}$ | $\overline{C}$ | $\overline{\Delta}$ C − B | B/C |
| Treatment Day | 1 | 36 | 33 | 337.9 | 422.1 | 84.2 | .804 |
| | 2 | 36 | 32 | 320.4 | 422.1 | 101.7 | .758 |
| | 3 | 36 | 36 | 295.0 | 422.1 | 127.1 | .704 |
| Average | | 36 | 36 | 317.8 | 422.1 | 104.4 | .754 |

EXAMPLE II 400 mg. solutions of 70% isopropylalcohol containing 2% chlorpheniramine maleate were compared for antiperspirant efficacy with control compositions of 400 mg. solutions of witch hazel water (14% alcohol) using the axillae method substantially as described above on human subjects. The results of this test are shown in Table 4 below.

The total number of subjects tested was twenty-four; twelve males and twleve females. Data from the first day of testing is shown in column A and column B under the heading "Day 1". As before, columns A and B represent the net gain in milligrams of perspiration produced in the untreated antihistamine and control axillae.

On the second day of testing, the composition to be compared were applied to the subjects in accordance with the procedure set forth in Example I. However, in this case, secretions were collected on the second day and on this day only.

Column C under the heading "Day 2" represents the difference in milligrams of the net gain in perspiration between the axillae treated with the antihistamine containing composition and the control composition. As explained in Example I a positive number indicates a greater reduction in perspiration produced by the axillae treated with the antihistamine containing composition, while a negative (—) sign preceding the number indicates a greater reduction in the perspiration produced by the axillae treated with the control composition.

Column D under "Day 2" represents the percentage of perspiration reduction which the difference between the treated axillae and the control composition represents.

TABLE 4

COMPARATIVE EFFECTIVENESS OF COMPOSITION CONTAINING CHLORPHENIRAMINE MALEATE VS. CONTROL SOLUTION

| SUBJECT NO. | DAY 1 A mgs | DAY 1 B mgs | DAY 2 C mgs | DAY 2 D % |
|---|---|---|---|---|
| 1 | 320 | 387 | 117 | 31.283 |
| 2 | 390 | 381 | 85 | 19.953 |
| 3 | 380 | 375 | 57 | 12.051 |
| 4 | 323 | 324 | 65 | 20.570 |
| 5 | 277 | 323 | 36 | 12.766 |
| 6 | 393 | 362 | 136 | 42.633 |
| 7 | 333 | 338 | 11 | 3.143 |
| 8 | 372 | 302 | 82 | 24.118 |
| 9 | 312 | 341 | 38 | 10.555 |
| 10 | 467 | 447 | 157 | 43.611 |
| 11 | 396 | 369 | 103 | 28.065 |
| 12 | 393 | 282 | 25 | 9.158 |
| 13 | 402 | 403 | —5 | 1.408 |
| 14 | 831 | 891 | 295 | 27.315 |
| 15 | 450 | 427 | 129 | 27.101 |
| 16 | 319 | 365 | 55 | 14.589 |
| 17 | 320 | 336 | 72 | 24.828 |
| 18 | 423 | 436 | 146 | 31.398 |
| 19 | 486 | 412 | 52 | 14.130 |
| 20 | 937 | 1,004 | 500 | 35.894 |
| 21 | 395 | 485 | 195 | 47.677 |
| 22 | 433 | 393 | 40 | 9.132 |
| 23 | 444 | 349 | 53 | 12.559 |
| 24 | 355 | 403 | 120 | 29.056 |

As shown in the table, in nearly every case there was a significant decrease in the amount of perspiration produced by those axillae treated with the antihistamine composition compared to those treated with the control solutions.

The total number of subjects, number perspiring less on the treated axillae (T), mean amounts perspired on the treated (T) and untreated (U) axillae, the mean untreated-treated differences and mean treated/untreated ratios appear in Table 5.

TABLE 5

| | n | n T < U | $\overline{T}$ | $\overline{U}$ | $\overline{\Delta} \ \overline{U - T}$ | T/U |
|---|---|---|---|---|---|---|
| Control | 24 | 11 | 425.5 | 419.8 | —5.8 | 1.021 |
| Test | 24 | 22 | 342.1 | 444.5 | 102.4 | .779 |
| Test/Control | 24 | 22 | | | 108.2 | .761 |

As shown, treatment was significantly effective in reducing perspiration of both males and females.

EXAMPLE III 400 mg solutions of 70% alcohol containing 2% tripelennamine hydrochloride were compared for antiperspirant efficacy with 400 mg. solutions of witch hazel (14% alcohol) using the axillae method as described in Example II on twenty-four human subjects; twelve males and twelve females. The results from this test are shown in Table 6 below:

TABLE 6

| SUBJECT NO. | DAY 1 A mgs | DAY 1 B mgs | DAY 2 C mgs | DAY 2 D % |
|---|---|---|---|---|
| 1 | 399 | 368 | 68 | 19.967 |
| 2 | 399 | 385 | 22 | 5.962 |
| 3 | 306 | 314 | 95 | 32.095 |
| 4 | 430 | 420 | 66 | 17.553 |
| 5 | 377 | 396 | 188 | 48.205 |
| 6 | 354 | 346 | 83 | 24.198 |
| 7 | 448 | 496 | 85 | 20.732 |
| 8 | 461 | 445 | 56 | 16.918 |
| 9 | 358 | 327 | 45 | 11.250 |
| 10 | 368 | 527 | 326 | 50.000 |
| 11 | 822 | 1.098 | 209 | 20.591 |
| 12 | 413 | 480 | 215 | 43.967 |
| 13 | 384 | 388 | 36 | 8.955 |
| 14 | 348 | 395 | 93 | 24.603 |
| 15 | 426 | 474 | 85 | 18.124 |
| 16 | 279 | 323 | 170 | 37.862 |
| 17 | 406 | 460 | 223 | 51.740 |
| 18 | 376 | 396 | 93 | 24.409 |
| 19 | 1.271 | 505 | —136 | 20.268 |
| 20 | 453 | 441 | 33 | 7.639 |
| 21 | 483 | 435 | 108 | 29.670 |
| 22 | 307 | 306 | 108 | 35.762 |
| 23 | 299 | 311 | 116 | 32.493 |
| 24 | 335 | 396 | 184 | 44.552 |

The total number of subjects, number perspiring less on the treated (T) axilla, mean amounts perspired on the treated (T) and untreated (U) axillae, the mean untreated-treated differences and mean treated/untreated ratios appear in Table 7.

TABLE 7

| | n | n T < U | $\overline{T}$ | $\overline{U}$ | $\overline{\Delta} \ \overline{U - T}$ | T/U |
|---|---|---|---|---|---|---|
| Control | 24 | 14 | 437.6 | 434.7 | 2.9 | .983 |
| Test | 24 | 23 | 323.2 | 430.3 | 107.1 | .731 |
| Test/Control | 24 | 23 | | | 110.0 | .743 |

As shown, treatment was significantly effective in reducing perspiration of both males and females.

EXAMPLE IV

Further tests were conducted to determine the effectiveness of the antihistamine containing compositions under ambient conditions. These tests were designated ambient air tests.

Both male and female subjects who had abstained from using antiperspirants in the axillae for 10 days or more were employed as test subjects. On Day "O", the subjects were fitted with a preweighed absorbent halter and permitted to leave the laboratory for four hours. During this time, no restrictions were imposed upon the kinds or amounts or their activity. After four hours, they returned to the laboratory, and the halters were removed and weighed. The difference in weight was determined to be the amount of auxillary perspiration produced. The collection period was always 12:00 Noon to 4:00 P.M.

On treatment days, the subjects were treated under each axilla at 11:00 A.M. and the halters were fitted one hour later at 12:00 Noon. One axilla was treated with a solution of diphenhydramine hydrochloride in witch hazel (14% alcohol) in which the concentration of the diphenhydramine hydrochloride was varied and the other axilla was treated with a solution of witch hazel (14% alcohol) and served as the control. The axillae were treated one hour prior to starting the collection. Assignments of the samples tested were randomized. Application was by pump spray.

As before, the subjects were permitted to leave the laboratory for four hours with no restrictions placed upon the kinds or amounts of their activity.

At the end of the four hours, the halters were removed and weighted to determine the amount of perspiration produced.

(A) A solution of diphenhydramine hydrochloride was tested for antiperspirant efficacy, using the ambient air method on 10 human subjects. The solution contained 1% diphenhydramine hydrochloride in 200 mgs. witch hazel (14% alcohol). A solution of witch hazel (14% alcohol) was used as a control. The results of this test are shown in Table 8.

On the treatment day (indicated in Table 8 as Day T*), one axilla was treated with the antihistamine containing solution and the other axilla was treated with the control solution one hour prior to starting the collection. Applications of the test and control solutions were randomized. Axillae treated with the diphenhydramine hydrochloride containing solutions are indicated in the table by double asterisk **.

TABLE 8

| Subject # | Day O | | Day T* | |
|---|---|---|---|---|
| | Left Axilla | Right Axilla | Left Axilla | Right Axilla |
| 1 | 413 | 441 | 252** | 416 |
| 2 | 436 | 499 | 501 | 264** |
| 3 | 392 | 462 | 386 | 301** |
| 4 | 279 | 240 | 188** | 265 |
| 5 | 351 | 319 | 317 | 195** |
| 6 | 358 | 444 | 330 | 264** |
| 7 | 295 | 316 | 211** | 371 |
| 8 | 308 | 342 | 197** | 316 |
| 9 | 352 | 365 | 206** | 301 |
| 10 | 305 | 371 | 295 | 231** |

*Day T - one axilla treated with 200 mgs. 1% diphen hydramine hydrochloride in witch hazel (14% alcohol); the other axilla treated with witch hazel (14% alcohol) 1 hour prior to starting collection.
**Axilla treated with diphenhydramine hydrochloride.

(B) A solution of 400 mgs. of witch hazel (14% alcohol) containing 2% diphenhydramine hydrochloride was tested for antiperspirant efficacy on human subjects using the ambient air method as described above. The results are represented in Table 9 below.

TABLE 9

| Subject # | Day O | | Day T* | |
|---|---|---|---|---|
| | Left Axilla | Right Axilla | Left Axilla | Right Axilla |
| 1 | 274 | 358 | 285 | 201** |
| 2 | 360 | 390 | 345 | 180** |
| 3 | 383 | 393 | 130** | 387 |
| 4 | 469 | 419 | 412 | 116** |
| 5 | 462 | 521 | 200** | 481 |
| 6 | 371 | 366 | 90** | 312 |
| 7 | 374 | 462 | 216** | 517 |
| 8 | 331 | 439 | 375 | 211** |
| 9 | 245 | 277 | 8** | 361 |
| 10 | 318 | 391 | 424 | 160** |

*Day T - one axilla treated with 400 mgs. 2% diphenhydramine hydrochloride in Witch Hazel (14% alcohol); the other axilla treated with Witch Hazel 1 hour prior to starting collection.
**Axilla treated with diphenhydramine hydrochloride.

(C) A solution of 400 mgs. of witch hazel (14% alcohol) containing 1% diphenhydramine hydrochloride was tested for antiperspirant efficacy, using the ambient air method. The procedure followed was substantially as before; however, in this particular test, 20 subjects were used and treatment of the axillae was made on two separate days. As before, a solution of witch hazel (14% alcohol) served as a control. The results are shown in Table 10.

TABLE 10

| Subjects # | Day O | | Day $T_1$* | | Day $T_2$* | |
|---|---|---|---|---|---|---|
| | Left Axilla | Right Axilla | Left Axilla | Right Axilla | Left Axilla | Right Axilla |
| 1 | 391 | 403 | 371 | 201** | 384 | 194** |
| 2 | 274 | 317 | 80** | 343 | 60** | 353 |
| 3 | 384 | 361 | 158** | 390 | 167** | 461 |
| 4 | 295 | 381 | 311 | 140** | 330 | 126** |
| 5 | 417 | 482 | 396 | 121** | 327 | 78** |
| 6 | 381 | 431 | 101** | 462 | 116** | 374 |
| 7 | 362 | 412 | 138** | 398 | 127** | 384 |
| 8 | 296 | 342 | 302 | 134** | 279 | 130** |
| 9 | 360 | 384 | 412 | 104** | 318 | 91** |
| 10 | 323 | 374 | 162** | 333 | 138** | 346 |
| 11 | 374 | 396 | 337 | 15%** | 362 | 147** |
| 12 | 416 | 441 | 54** | 401 | 36** | 412 |
| 13 | 312 | 392 | 306 | 162** | 347 | 176** |
| 14 | 274 | 316 | 291 | 78** | 287 | 48** |
| 15 | 337 | 301 | 106** | 348 | 100** | 332 |
| 16 | 410 | 395 | 351 | 118** | 363 | 92** |
| 17 | 367 | 411 | 309 | 129** | 324 | 102** |
| 18 | 296 | 327 | 88** | 366 | 62** | 383 |
| 19 | 384 | 368 | 162** | 401 | 137** | 319 |
| 20 | 301 | 373 | 128** | 323 | 101** | 368 |

*Day $T_1$ and $T_2$ - one axilla treated with 400 mgs. 1% diphenhydramine hydrochloride in witch hazel (14% alcohol); the other axilla treated with witch hazel 1 hour prior to starting collection.
**Axilla treated with diphenhydramine hydrochloride.

In summary, the ambient air tests showed very marked reductions in perspiration following application of diphenhydramine hydrochloride (in 1% and 2% solutions). Each of the twenty panelists tested the product two separate weeks. All twenty panelists experienced a reduction of perspiration of at least 29% following one application the first week and at least 49% following two applications the second week.

Mean amounts perspired on the diphenhydramine hydrochloride in witch hazel [1% (A) and 2% (B)] and witch hazel axillae (C) on control and treatment days, mean differences, mean A/C and B/C ratios and number of panelists perspiring less on the treated (to be treated on control days) axillae appear in Table 11.

TABLE 11

| (A) 1% Solution | | | | | | |
|---|---|---|---|---|---|---|
| | n | n A < C | $\overline{A}$ | $\overline{C}$ | Δ C − A | A/C |
| Control 8/12 | 10 | 5 | 374.2 | 354.6 | −19.6 | 1.050 |
| Test 1 8/13 | 10 | 10 | 230.9 | 349.8 | 118.9 | .663 |
| Test/Control | 10 | 10 | | | 138.5 | .632 |

| (B) 2% Solution | | | | | | |
|---|---|---|---|---|---|---|
| | n | n B < C | $\overline{B}$ | $\overline{C}$ | Δ C − B | B/C |
| Control 8/5 | 10 | 5 | 383.2 | 377.1 | −6.1 | 1.026 |
| Test 1 8/7 | 10 | 10 | 151.2 | 390.0 | 238.7 | .310 |
| Test/Control | 10 | 10 | | | 244.8 | .302 |

| (C) 1% Solution | | | | | | |
|---|---|---|---|---|---|---|
| | n | n A < C | $\overline{A}$ | $\overline{C}$ | Δ C − A | A/C |
| Control | 10 | 6 | 357.9 | 371.8 | 13.9 | .962 |
| Test 1 | 10 | 10 | 126.4 | 365.7 | 239.3 | .343 |
| Test 1/Control | 10 | 10 | | | 225.4 | .356 |
| Test 2 | 10 | 10 | 109.6 | 345.8 | 236.2 | .310 |
| Test 1-2 | 10 | 10 | 118.0 | 355.8 | 237.8 | .326 |
| Test 1-2/Control | 10 | 10 | | | 223.8 | .339 |
| [Group from (A)]* | | | | | | |
| Control | 10 | 2 | 378.1 | 348.3 | 29.8 | 1.087 |
| Test 1 | 10 | 10 | 125.8 | 349.4 | 223.6 | .338 |

TABLE 11-continued

| | n | n A<C | $\bar{A}$ | $\bar{C}$ | Δ C−A | A/C |
|---|---|---|---|---|---|---|
| Test 1/Control | 10 | 10 | | | 253.4 | .311 |
| Test 2 | 10 | 10 | 113.2 | 359.4 | 246.2 | .276 |
| Test 1-2 | 10 | 10 | 119.5 | 354.9 | 234.9 | .305 |
| Test 1-2/Control | 10 | 10 | | | 264.7 | |

[Group from (B)]*

| | n | n A<C | $\bar{A}$ | $\bar{C}$ | Δ C−A | A/C |
|---|---|---|---|---|---|---|
| Control | 20 | 8 | 368.0 | 360.0 | −8.0 | 1.022 |
| Test 1 | 20 | 20 | 126.1 | 357.6 | 231.5 | .340 |
| Test/Control | 20 | 20 | | | 239.5 | .333 |
| Test 2 | 20 | 20 | 111.4 | 352.6 | 241.2 | .293 |
| Test 1-2 | 20 | 20 | 118.8 | 355.1 | 236.3 | .316 |
| Test/Control | 20 | 20 | | | 244.3 | .309 |

[Total]*

*In Table 11, the report of the 1% solution test in (C) is separated into those same subjects tested with the 1% solution previously [group from (A)], those previously treated with the 2% solution [group from (B)], and the subjects from both groups together [Total].

Both the one and two percent concentrations of diphenhydramine hydrochloride provide significantly effective in reducing perspiration. The drug evoked an unusual unanimity of response; every panelist experienced a decrease in perspiration on every day.

The minimum drop among the ten panelists testing the 2% percent concentration was 46%. The minimum drop of those testing the 1% concentration was 29%. While the 2% drops exceeded the 1% drops significantly, the effects of concentrations and variations in ambient temperature on days tested cannot be separated.

When all twenty panelists tested the one percent concentration simultaneously, the minimum drop following one application was 43% and 49% following the second application. The second test day was significantly more effective than the first day.

Anti-perspirant compositions were formulated by combining the following ingredients. The examples shown are merely illustrative and are not to be construed as a limitation of the invention. One skilled in the art will be able to make such variations, substitutions and changes in the ingredients and parameters as may seem desirable.

EXAMPLE V

Antiperspirant Cream

| INGREDIENTS | % BY WEIGHT | | | |
|---|---|---|---|---|
| | A | B | C | D |
| Diphenhydramine HCl | 1.0 | 1.0 | 1.0 | 1.0 |
| Aluminum chlorohydrate, 50% aqueous solution | — | 40.0 | 32.0 | 32.0 |
| Aluminum chloride hexahydrate, 50% aqueous solution | — | — | 6.0 | — |
| Aluminum sulfate | — | — | — | 8.0 |
| Isopropl myristate | 200 | 2.0 | 2.0 | 2.0 |
| Glyceryl monostearate (non-self emulsifying) | 12.0 | 8.0 | 8.0 | 8.0 |
| *Promulgen G. (Robinson Wagner Co.) | 5.0 | 5.0 | 8.0 | 8.0 |
| Propylene glycol | 5.0 | 5.0 | 5.0 | 5.0 |
| Titanium dioxide | 0.5 | 0.5 | 0.5 | 0.5 |
| Perfume | 0.2 | 0.2 | 0.2 | 0.2 |
| Water, deionized | 74.2 | 38.3 | 35.3 | 3303 |
| Glycine | — | — | 2.0 | 2.0 |
| Methyl paraben | 0.25 | — | — | — |
| propyl paraben | 0.05 | — | — | — |
| | 100.0 | 100.0 | 100.0 | 100.0 |

When applied to the axilla as shown in the axilla test, above, perspiration of the subject is effectively reduced.

In the above formulation diphenhydramine was replaced by chlorpheniramine maleate. The same results are obtained.

Likewise with tripelennamine hydrochloride when using the ambient method good control is evident.

Subjects treated with phenyltoloxamine observe a decrease in perspiration.

In the cream formulation above, diphenhydramine HCl is reduced to an amount of 0.01%. Reduction in sweating is observed in the subject.

In the cream formulation, the salt proportion is reduced to 0.5%. The treated subjects observe a reduction of sweating in the axilla method.

In the cream, the amount of aluminum salts was reduced to total 0.5%. This is an amount which is generally inadequate to reduce sweating when used alone. Subjects using the cream observe satisfactory control of sweating both in the axilla and ambient air methods, repeating the tests described above. Sweating was also decreased after the second application, during the second day.

EXAMPLE VI

Antiperspirant Roll-on (Emulsion)

| INGREDIENTS | % BY WEIGHT | | | | | |
|---|---|---|---|---|---|---|
| | A | B | C | D | E | F |
| Diphenhydramine HCl | 1.0 | 1.0 | 1.0 | 1.0 | 1.0 | 1.0 |
| Aluminum chlorohydrate | — | — | 22.0 | 16.0 | — | — |
| Aluminum chloride hexahydrate | — | — | — | 3.0 | 10.0 | — |
| Aluminum sulfate | — | — | — | — | — | 10.0 |
| Glycine | — | — | — | 2.0 | 2.0 | 2.0 |
| Isopropyl myristate | 3.0 | — | — | — | — | — |
| Glyceryl monostearate, (non-self-emulsifying) | 6.0 | 5.0 | 5.0 | 5.0 | 5.0 | 5.0 |
| Brij 72 (ICI) | 1.5 | — | — | — | — | — |
| Brij 78 (ICI) | 2.5 | — | — | — | — | — |
| Brij 30 (ICI) | — | 1.5 | 1.5 | 1.5 | 1.5 | 1.5 |
| Brij 35 (ICI) | — | 2.5 | 2.5 | 2.5 | 2.5 | 2.5 |
| Methocel 60 EG 4000 CPS (Dow Chemical) | — | 0.3 | — | — | — | — |
| Propyl paraben | 0.05 | 0.05 | — | — | — | — |
| Methyl paraben | 0.25 | 0.25 | — | — | — | — |
| Water, deionized | 85.70 | 89.40 | 68.0 | 69.0 | 78.0 | |
| | 100.0 | 100.0 | 100.0 | 100.0 | 100.0 | 100.0 |

Effective perspiration reduction is evidenced in subjects when the emulsion formulation is applied in the axilla test as described. In the above formulation diphenhydramine was replaced by chlorpheniramine maleate in the axillary method and tripelennamine hydrochloride when using the ambient method. Sweating was controlled over several days.

Subjects treated with methapyrilene also observed a decrease in perspiration.

In the emulsion formulation above, diphenhydramine HCl is reduced to an amount of 0.01%, with reduction in sweating observed in the subject.

In the emulsion formulation, the salt proportion is reduced to 0.5%. The subjects so treated also observe a reduction of sweating in the axilla method.

The amount of aluminum sulfate was reduced to total 0.5% with similar results.

Subjects using the roll-on observed satisfactory control of sweating, repeating the tests described above. Sweating was also decreased after the second application, during the second day.

EXAMPLE VII

Antiperspirant Pump Spray

| INGREDIENTS | % BY WEIGHT | | | |
|---|---|---|---|---|
| | A | B | C | D |
| Diphenhydramine HCl | 1.0 | 1.0 | 1.0 | 1.0 |
| *Rehydrol (Reheis Chemical Co.) | — | 15.0 | — | — |
| Aluminum chlorohydrate | — | — | 10.0 | 10.0 |
| Aluminum chloride hexahydrate | — | — | — | 1.0 |
| Propylene glycol | — | — | 2.0 | 2.0 |
| Perfume | — | 0.3 | 0.3 | 0.3 |
| Alcohol, 95% | 70.0 | 83.7 | 51.5 | 50.5 |
| Water | 29.0 | — | 35.2 | 35.2 |
| | 100.0 | 100.0 | 100.0 | 100.0 |

Sweating is effectively reduced in subjects when the above formulation is applied to the axillae as shown in the axilla test above.

Diphenhydramine was replaced by chlorpheniramine maleate and by tripelennamine hydrochloride when using the ambient method. The same results are obtained.

Subjects treated with antihistamine free of astringent salts observed a decrease in perspiration as well.

In the spray formulation above, diphenhydramine HCl is reduced to an amount of 0.01%. Reduction in sweating is observed in the subject.

When 0.2% of aluminum chlorohydrate was added to the spray and the amount of antihistamine was reduced to 0.2% sweating is reduced in both males and females when tested in the ambient method.

The treated subjects observe a reduction of sweating in the axilla method when using an amount of the above salt which is generally inadequate to reduce sweating when used alone. Sweating was also satisfactorily decreased after the second application, during the second day.

Application is also effectively made to the soles of the feet.

EXAMPLE VII

Antiperspirant Solutions (Pads & Dab-o-matics)

| INGREDIENTS | PERCENT BY WEIGHT | | | | |
|---|---|---|---|---|---|
| | A | B | C | D | E |
| Diphenhydramine HCl | 1.0 | 1.0 | 1.0 | 1.0 | 1.0 |
| Aluminum chlorohydrate | — | 22.0 | 16.0 | — | — |
| Aluminum chloride hexahydrate | — | — | 3.0 | 10.0 | — |
| Aluminum sulfate | — | — | — | — | 10.0 |
| Glycine | — | — | 1.0 | 3.0 | — |
| Propylene glycol | 5.0 | 5.0 | 5.0 | 5.0 | 5.0 |
| Alcohol, 95% | 30.0 | 30.0 | 31.0 | 30.0 | 32.0 |
| Water, Deionized | 64.0 | 42.0 | 43.0 | 51.0 | 52.0 |
| | 100.0 | 100.0 | 100.0 | 100.0 | 100.0 |

When using the solution formulation, subjects observed satisfactory control of sweating in the axilla and ambient air test methods.

This is also seen when diphenhydramine is replaced by chlorpheniramine maleate, brompheniramine or with tripelennamine hydrochloride when using the ambient method. The subjects experienced a reduction in sweating with 0.5% of the antihistamine.

The diphenhydramine may be used free of its acid addition salt.

In the solution formulation above, diphenhydramine HCl is reduced to an amount of 0.01%. Perspiration of the subject is effectively reduced.

In the solution formulation, the salt proportion is reduced to 0.1%. The treated subjects observe similarly effective results.

In the solution, the aluminum salts were replaced by zirconium salts. Subjects using the cream observed satisfactory control of sweating both in the axilla and ambient air methods, repeating the tests described above. Sweating was also decreased after the third application, during the third day.

EXAMPLE IX

Antiperspirant Stick

| INGREDIENTS | % BY WEIGHT | | | | |
|---|---|---|---|---|---|
| | A | B | C | D | E |
| Aluminum chlorohydrate (impalpable powder) | — | 22.0 | 16.0 | — | — |
| Aluminum chloride hexahydrate | — | — | 3.0 | 10.0 | — |
| Diphenhydramine HCl | 1.0 | 1.0 | 1.0 | 1.0 | 1.0 |
| Aluminum sulfate | — | — | — | — | 10.0 |
| Glycine | — | — | — | 4.0 | — |
| Isopropyl myristate | 10.0 | 10.0 | 10.0 | 10.0 | 5.0 |
| Perfume | 1.0 | 1.0 | 1.0 | 1.0 | 1.0 |
| Ozokerite wax 170 (Melting Point 170° F. Penick Co.) | 6.0 | 6.0 | 6.0 | 6.0 | 6.0 |
| Stearyl alcohol | 11.5 | 11.5 | 11.5 | 11.5 | 11.5 |
| Silicone fluid #251 (Stauffer) | 70.5 | 48.5 | 51.5 | 56.5 | 65.5 |
| | 100.0 | 100.0 | 100.0 | 100.0 | 100.0 |

In the above formulation diphenhydramine was replaced by chlorpheniramine maleate and with tripelennamine hydrochloride when using the ambient method. Tripelennamine is used free of its acid addition salt, as well. When applied to the axilla as shown in the axilla test, above, perspiration of the subject is effectively reduced.

Use of pyrilamine maleate also results in a decrease in perspiration.

In the stick formulation above, diphenhydramine HCl is reduced to an amount of 0.01%. Reduction in sweating is observed in the subject.

When the salt proportion is reduced to 0.5%, treated subjects observe a reduction of sweating in the axilla method. Hafnium salts are also used in lieu of aluminum salts.

Sweating was decreased after further application, during the second and third days.

EXAMPLE X

Aerosol Antiperspirant Solution Spray

| INGREDIENTS | % BY WEIGHT | | |
|---|---|---|---|
| | A | B | C |
| Diphenhydramine HCl | 1.0 | 5.0 | 1.0 |
| *Rehydrol (Reheis Chemical Co.) | — | 5.0 | — |
| Alcohol, anhydrous | 50.0 | 50.0 | 92.0 |
| Isopropyl myristate | 2.0 | 2.0 | 2.0 |
| Propellant 12 | 28.2 | 25.2 | — |
| Propellant 11 | 18.8 | 16.8 | — |
| Carbon dioxide | — | — | 5.0 |
| | 100.0 | 100.0 | 100.0 |

*CTFA Aluminum chlorohydrex

In the above formulation diphenhydramine was used in combination with chlorpheniramine maleate and alternatively with tripelennamine hydrochloride when using the ambient method. The same results are obtained, sweating is effectively reduced in subjects tested.

Effective perspiration control is also observed in subjects treated with promethazine.

In the solution spray formulation above, diphenhydramine HCl is reduced to an amount of 0.01%. Reduction in sweating is observed in the subject.

In the solution spray, the antihistamine may be used free of the astringent metal salt. The treated subjects observe a reduction of sweating in the axilla method.

In the solution spray, the amount of aluminum salts was reduced to total 0.1%. This amount is generally inadequate to reduce sweating when used alone.

Sweating was further decreased after subsequent applications during testing.

EXAMPLE XI

Aerosol Antiperspirant Suspension Spray

| INGREDIENTS | PERCENT BY WEIGHT | | | |
|---|---|---|---|---|
|  | A | B | C | D |
| Diphenhydramine HCl | 1.0 | 1.0 | 1.0 | 1.0 |
| Aluminum chlorohydrate (impalpable powder) | — | — | 3.5 | 3.5 |
| Aluminum chloride hexahydrate | — | — | — | 0.5 |
| Cab-O-Sil M-5 (Cabot Corp.) | 0.2 | 0.2 | 0.2 | 0.2 |
| Isopropyl myristate | 2.0 | 5.0 | 5.0 | 5.0 |
| Talc 2755 (Whittaker C&D) | 2.0 | — | — | — |
| Glycine, USP | — | — | — | 0.5 |
| Perfume | 0.2 | 0.2 | 0.2 | 0.2 |
| Propellant 12 | 33.1 | 32.8 | 31.5 | 31.2 |
| Propellant 11 | 61.5 | 60.8 | 58.6 | 57.9 |
|  | 100.0 | 100.0 | 100.0 | 100.0 |

When applied to the axilla as shown in the axilla test, above, perspiration of the subject is effectively reduced.

In the above formulation diphenhydramine was used together with chlorpheniramine maleate and with tripelennamine hydrochloride and chlorpheniramine maleate when using the ambient method. Subjects observed reduction of perspiration in the axilla test.

Subjects treated with clemizone observe a decrease in perspiration.

In the formulation above, diphenhydramine HCl is reduced to an amount of 0.01%. Reduction in sweating is observed in the subject.

In the formulation, the salt proportion is reduced to 0.1%. The treated subjects observe a reduction of sweating in the axilla method.

In the suspension spray, the aluminum chlorhydrate is present at 0.1% and satisfactory control of sweating both in the axilla and ambient air methods occurs.

Sweating was also decreased after the second application, during the second day.

In the above examples, ingredients other than those recited can be added to achieve a cosmetically desirable product. The physical form of the product can be any of those known to the cosmetic art.

We claim:

1. An antiperspirant composition useful for prophylactic control of sweating of generally unexposed areas of the body subject to sweating in humans, comprising an antihistamine selected from the group consisting of an ehtanolamine, an ethylenediamine, an alkylamine, a phenothiazine and piperazine, or physiologically acceptable salt thereof, in conjunction with a metal salt having astringent properties and a pharmaceutically acceptable carrier, the combined amounts of antihistamine and of the metal salt act together to produce a synergistic effect and being in an amount effective to control perspiration.

2. The composition of claim 1 wherein the antihistamine is chlorpheniramine.

3. The composition of claim 1 wherein the antihistamine is diphenhydramine.

4. The composition of claim 1 wherein the antihistamine is triplennamine.

5. The composition of claim 1 wherein the amount of antihistamine is at least about 1%.

6. The method of controlling perspiration which comprises administering topically to a human, a synergistic antiperspirant composition comprising an antihistamine selected from the group consisting of an ethanolamine, an ethylenediamine, an alkylamine, a phenothiazine and a piperazine, or a physiologically acceptable salt thereof, in conjunction with a metal salt having astringent properties, and a pharmaceutically acceptable carrier, the combined amounts of the antihistamine and the metal salt act together to produce a synergistic effect and being in an amount effective to control the perspiration.

7. The method of claim 6 wherein the administration is to the axillary area of the human body.

8. The method of claim 6 wherein the administration comprises applying the composition under conditions where no sweating is occuring, then subjecting the area so treated to conditions of heat which induce sweating and inhibiting sweating under such conditions.

9. The method of claim 6 wherein the administration is prophylactic.

10. The method of claim 9 wherein the administration is to the axillary area of the body.

11. The method of claim 6 wherein the metal salt is present in said antiperspirant composition in an amount less than that which is effective to be astringent to control perspiration when used alone.

12. The method of claim 6 wherein the metal salt is present in said antiperspirant composition in a range from a small but perceptible amount to about 2% by weight.

13. The method of claim 11 wherein the metal salt is present in said antiperspirant composition in an amount in the range of about 0.1% to about 1% by weight.

14. The method in claim 6 wherein the antihistamine is present in said antiperspirant composition in an amount less than that which is effective to control perspiration when used alone.

15. The method of claim 6 wherein the antihistamine is present in said antiperspirant composition in a small but perceptible amount to about 10% by weight.

16. The method of claim 6 wherein the antihistamine is present in said antiperspirant composition in an amount in the range of about 0.01% to about 5% by weight.

17. The method in claim 6 wherein the antihistamine is present in said antiperspirant composition in an amount in the range of about 0.01% to about 2% by weight.

18. The method of claim 6 wherein the controlling is the reduction of perspiration.

19. The method of claim 14 wherein the reduction of perspiration is carried out over a plurality of days.

20. The method of claim 15 wherein during that period the treated area is exposed to washing.

21. The method of claim 10 wherein the administration is by spray.

* * * * *